(12) United States Patent
Torabi et al.

(10) Patent No.: US 12,207,861 B2
(45) Date of Patent: Jan. 28, 2025

(54) REAL-TIME SURGICAL TOOL PRESENCE/ABSENCE DETECTION IN SURGICAL VIDEOS

(71) Applicant: Verb Surgical Inc., Santa Clara, CA (US)

(72) Inventors: Meysam Torabi, Union City, CA (US); Varun Kejriwal Goel, Santa Clara, CA (US); Danyal Fer, Oakland, CA (US); Jocelyn Barker, San Jose, CA (US); Amer Ghanem, Santa Clara, CA (US); Richard W. Timm, Cincinnati, OH (US)

(73) Assignee: Verb Surgical Inc., Santa Clara, CA (US)

( * ) Notice: Subject to any disclaimer, the term of this patent is extended or adjusted under 35 U.S.C. 154(b) by 400 days.

(21) Appl. No.: 17/566,116

(22) Filed: Dec. 30, 2021

(65) Prior Publication Data

US 2023/0210579 A1    Jul. 6, 2023

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1445* (2013.01); *A61B 18/1482* (2013.01);
(Continued)

(58) Field of Classification Search
CPC ............ A61B 18/1233; A61B 18/1445; A61B 18/1482; A61B 2018/00595; A61B 2018/00601; A61B 2018/0063; A61B 2018/00672; A61B 2018/00678; A61B 2018/00898; A61B 2018/00982; A61B 2018/00994; A61B 2018/126;
(Continued)

(56) References Cited

U.S. PATENT DOCUMENTS

2017/0165013 A1* 6/2017 Itkowitz ................ A61B 90/37
2017/0367559 A1* 12/2017 Takahashi ............ A61B 5/0036
(Continued)

*Primary Examiner* — Jason Holloway
*Assistant Examiner* — Benjamin J Brosh
(74) *Attorney, Agent, or Firm* — Aikin & Gallant, LLP

(57) ABSTRACT

Embodiments described herein provide various techniques and systems for building machine-learning surgical tool presence/absence detection models for processing surgical videos and predicting whether a surgical tool is present or absent in each video frame of a surgical video. In one aspect, a process for ensuring patient safety during a laparoscopic or robotic surgery involving an energy tool is disclosed. The process can begin receiving a real-time control signal indicating an operating state of an energy tool during the surgery. Next, the process receives real-time endoscope video images of the surgery. The process simultaneously applies a machine-learning surgical tool presence/absence detection model to the real-time endoscope video images to generate real-time decisions on a location of the energy tool in the real-time endoscope video images. The process then checks the real-time control signal against the real-time decisions to identify an unsafe event and takes a proper action when an unsafe event is identified.

13 Claims, 8 Drawing Sheets

(51) Int. Cl.
  *A61B 34/30* (2016.01)
  *G06N 3/0464* (2023.01)
  *G06N 3/08* (2023.01)
  *G06N 3/09* (2023.01)
  *G06N 20/00* (2019.01)
  *G16H 20/40* (2018.01)
  *A61B 18/00* (2006.01)
  *A61B 34/20* (2016.01)
  *G06T 7/00* (2017.01)

(52) U.S. Cl.
  CPC ........... *A61B 34/30* (2016.02); *G06N 3/0464* (2023.01); *G06N 3/08* (2013.01); *G06N 3/09* (2023.01); *G06N 20/00* (2019.01); *G16H 20/40* (2018.01); *A61B 2018/00595* (2013.01); *A61B 2018/00601* (2013.01); *A61B 2018/0063* (2013.01); *A61B 2018/00672* (2013.01); *A61B 2018/00678* (2013.01); *A61B 2018/00898* (2013.01); *A61B 2018/00982* (2013.01); *A61B 2018/00994* (2013.01); *A61B 2018/126* (2013.01); *A61B 2034/2065* (2016.02); *G06T 7/00* (2013.01)

(58) Field of Classification Search
  CPC  A61B 2018/00642; A61B 2018/00666; A61B 2090/3612; A61B 34/37; A61B 2034/2065; G06N 20/00; G06N 3/0464; G16H 20/40; G16H 40/20; G16H 40/40; G16H 50/50; G16H 30/40; G16H 40/63; G06Q 10/0635; G06Q 10/06398; G06Q 50/22

See application file for complete search history.

(56) References Cited

U.S. PATENT DOCUMENTS

| | | | |
|---|---|---|---|
| 2021/0015554 A1* | 1/2021 | Chow | A61B 17/320092 |
| 2021/0307841 A1* | 10/2021 | Buch | A61B 5/749 |
| 2022/0104884 A1* | 4/2022 | Leiderman | A61B 1/000095 |
| 2022/0202490 A1* | 6/2022 | Hancock | A61B 8/12 |
| 2022/0313388 A1* | 10/2022 | Tamarozzi | G06V 20/00 |
| 2022/0346884 A1* | 11/2022 | Leiderman | G16H 30/40 |
| 2023/0263587 A1* | 8/2023 | Pandya | A61B 34/77 606/1 |

* cited by examiner

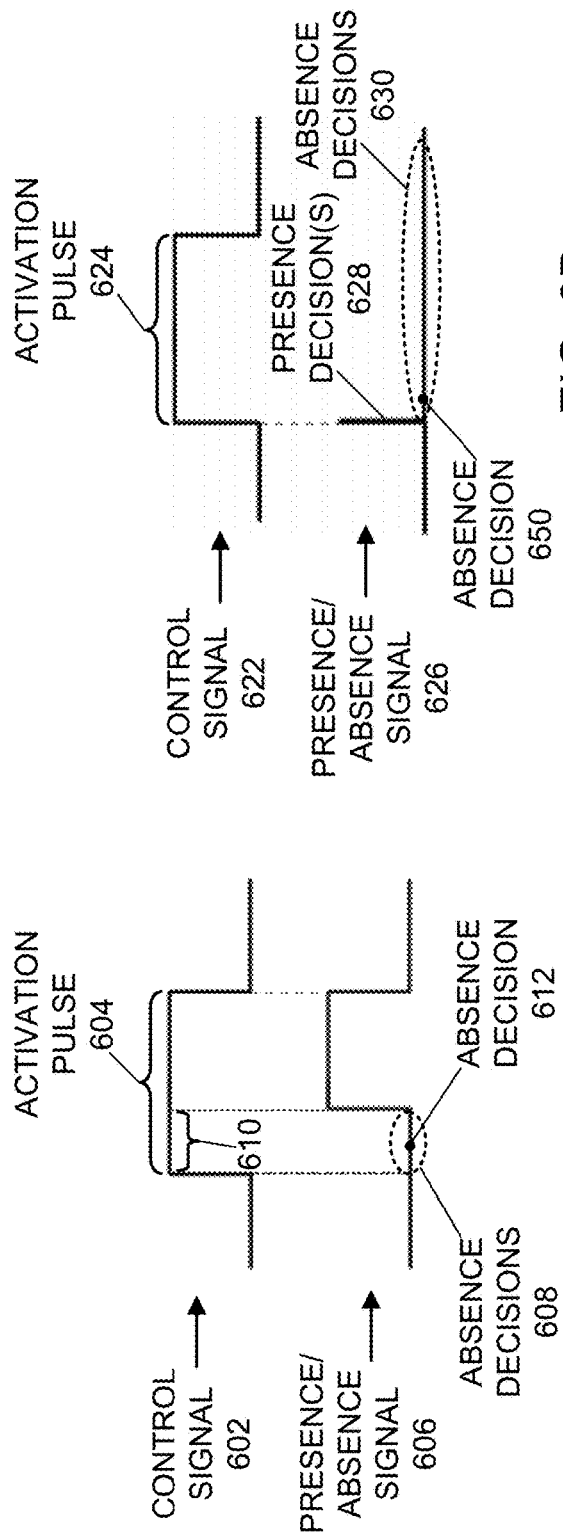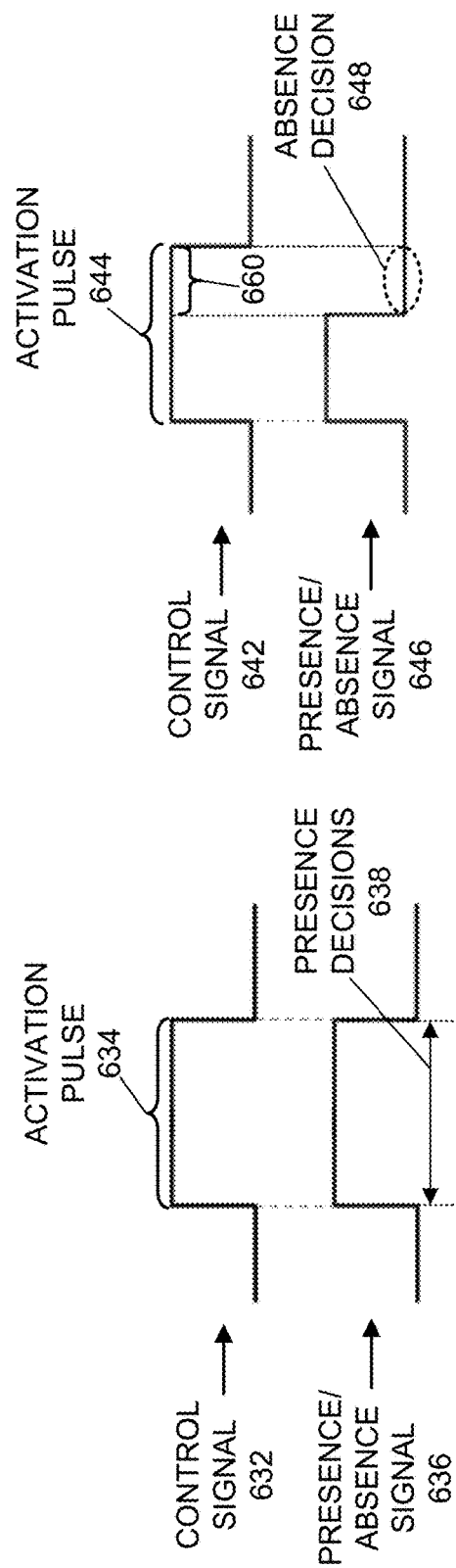

REAL-TIME SURGICAL TOOL PRESENCE/ABSENCE DETECTION IN SURGICAL VIDEOS

TECHNICAL FIELD

The disclosed embodiments generally relate to providing machine-learning solutions to assist and improve surgeries. More specifically, the disclosed embodiments relate to building real-time machine-learning surgical tool presence/absence detectors and detecting surgical tool presence/absence in surgical videos.

BACKGROUND

Surgical videos contain highly valuable and rich information for real-time event detections, and off-line training, assessing and analyzing the quality of the surgeries and skills of the surgeons, and for improving the outcomes of the surgeries and skills of the surgeons. There are many surgical procedures which involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many surgical procedures, e.g., a gastric sleeve or cholecystectomy, a large cache of surgical videos already exist and continue to be created as a result of a large number of surgical cases performed by many different surgeons from different hospitals.

Surgical videos provide excellent visual feedback to track the usages of surgical tools during laparoscopic surgeries as well as robotic surgeries. Machine-learning tool detection and tracking solutions have been developed to leverage surgical videos to extract useful information, such as detecting which surgical tools have been used and how often each surgical tool has been used during a surgery to enable various clinical applications. Another important use case of surgical videos is to detect improper usage or handling of energy tools/devices that can cause injuries to the patients during surgeries. This requires building real-time energy tool/device and related unsafe event detection mechanisms. However, most of the energy tool manufacturers do not offer such safety features in their products.

Hence, what is needed is an energy tool/device unsafe usage monitoring technique without the drawbacks of existing systems.

SUMMARY

Embodiments described herein provide various techniques and systems for building machine-learning (ML)/deep-learning (DL) surgical tool detection models for processing surgical videos and predicting whether a surgical tool is present or absent in each video frame of a surgical video. In particular, the ML surgical tool detection models described in this disclosure include an energy tool presence/absence detection model which is trained and used to process a real-time surgical video of a laparoscopic or robotic surgery that uses an energy tool to cut and cauterize/seal tissues, and generate a real-time prediction for each video frame regarding whether the energy tool is present or absent in each video frame.

In various embodiments, the disclosed energy tool presence/absence detection model is built to detect multiple models and versions of a given type of the energy tool instead of a particular model or version of the given type of the energy tool. In some embodiments, a disclosed energy tool presence/absence detection model is built for various models and versions of an ultrasonic energy tool by one manufacturer, such as Harmonic™ scalpels by Ethicon™. However, a separate energy tool presence/absence detection model may be built for various models and versions of an ultrasonic energy tool by another manufacturer, such as Sonicision™ scalpels by Covidien™. Another disclosed energy tool presence/absence detection model can be built for various models and versions of a bipolar energy tool by one manufacturer, such as Enseal™ tissue sealers by Ethicon™. However, a separate energy tool presence/absence detection model may be built for various models and versions of a bipolar energy tool by another manufacturer, such as a Ligasure™ tissue sealers by Covidien™. The disclosed energy tool presence/absence detection model is further integrated with an energy-tool unsafe-use detection process to detect unsafe events associated with the energy tool usage during a surgery and to prevent injuries from the energy tool.

In various embodiments, the disclosed ML surgical tool detection model building techniques and systems can build a robust surgical tool detection model by first obtaining an initially trained tool detection model based on an initial training dataset, wherein the initial training dataset can include collected images of the surgical tool in different types and models, instead of just a particular type/model of the energy tool. This will allow building an initially trained tool detection model that can cover all types and models of the energy tool that are potentially in use everywhere. To increase training data diversity to cover more real-world scenarios, multiple data augmentation techniques including random color distortion and geometrical transformation can be carefully applied to the initial training dataset, while keeping the original labels of the images. The extended training dataset including both the initial training dataset and the augmented versions of the initial training images can be used to train an initial ML tool detection model and obtain the initially trained tool detection model.

The disclosed ML surgical tool detection model building techniques and systems also include mechanisms to update or further train the initially trained tool detection model based on additional training images related to the energy tool and energy tool usage. In some embodiments, the disclosed ML surgical tool detection model building techniques and systems update the initially trained tool detection model through the active learning, which can involve a training loop. This includes using the initially trained tool detection model to separate the additional training images into high-confidence-level images that are similar to images in the initial training dataset; and low-confidence-level images that are significantly different from images in the initial training dataset. The identified low-confidence-level images are then annotated by skilled annotators. Next, the disclosed ML surgical tool detection model building techniques and systems trains/updates the initially trained tool detection model using the labeled low-confidence-level images to update. The updated surgical tool detection model can have improved accuracy and precision than the initially trained tool detection model, and can also detect more diverse and more complex surgical scenarios related to the surgical tool than the initially trained tool detection model.

Using the disclosed surgical tool detection model updating techniques, the initially trained tool detection model is updated on a significantly smaller but information-rich set of additional training images, which makes the model training/updating process much more efficient than using both high-confidence-level images and low-confidence-level images. Moreover, the convergence time during the model optimization is greatly reduced comparing with a training process without using active learning when the same validation dataset is used. Note that the disclosed ML surgical tool detection model building techniques and systems can be used not only to build energy tool present/absent detection models, but also to build surgical tool detection models for surgical tools other than energy tools.

In one aspect, a process for ensuring patient safety during a laparoscopic or robotic surgery involving an energy tool is disclosed. The process can begin receiving a real-time control signal indicating an operating state of an energy tool during the surgery. Next, the process receives real-time endoscope video images of the surgery. The process simultaneously applies a machine-learning model to the real-time endoscope video images to generate real-time decisions on a location of the energy tool in the real-time endoscope video images. The process then checks the real-time control signal against the real-time decisions to identify an unsafe event and takes a proper action when an unsafe event is identified.

In some embodiments, the tool control signal includes a plurality of activation pulses, and each activation pulse in the plurality of activation pulses corresponds to a time duration when the energy tool is activated.

In some embodiments, the process applies the machine-learning model to the real-time endoscope video images to generate the real-time decisions by: for each video frame in the real-time endoscope video images, processing the video frame using the machine-learning model to generate a tool presence/absence decision indicating whether the energy tool is present or absent in the video frame and a confidence level associated with the presence/absence decision.

In some embodiments, the energy tool is an ultrasonic energy tool for cutting and sealing tissues at the same time using two jaws, and wherein the machine-learning model is trained to generate a tool presence decision for the video frame only when both of the two jaws are detected in the video frame.

In some embodiments, the process checks the tool signal against the real-time decisions to identify an unsafe event by first determining that a newly-generated decision is a tool absence decision. Next, the process determines if the tool absence decision coincides with an activation pulse in the tool signal. If so, the process further determines if the tool absence decision is at the beginning of the time duration of activation. If so, the process determines that an unsafe event is identified. However, if the tool absence decision is not at the beginning of the time duration of activation, the process determines that the energy tool is safe to use.

In some embodiments, if the tool absence decision does not coincide with any activation pulse in the tool signal, the process determines that the energy tool is safe to use.

In some embodiments, to take the proper action when an unsafe event is identified, the process further determines if the confidence level of the identified unsafe event is above a high confidence level threshold. If so, the process immediately disables the energy tool. However, if the confidence level of the identified unsafe event is below the high confidence level threshold, the process takes one or more actions selected from the following options without disabling the energy tool: (1) displaying a visual alert on an endoscope monitor; (2) generating an audio alert; (2) generating a mechanical vibration through the energy tool; and (4) delaying the firing of the energy tool until the user takes a further action on the energy tool.

In another aspect, process for generating a surgical tool presence/absence detection model for detecting the presence or absence of a surgical tool in surgical video images is disclosed. The process may first receive an initial training dataset of labeled surgical video images, wherein each labeled video image in the initial training dataset is either labeled as a tool-absent image indicating the surgical tool is absent in the video image, or labeled as a tool-present image indicating the surgical tool is present in the video image. The process then trains a tool presence/absence detection model using the labeled training dataset to obtain a trained tool detection model, wherein the trained tool detection model is capable of classifying a surgical image as either a tool-absent image or a tool-present image. Next, the process applies the trained tool detection model to an additional dataset of surgical video images to identify a subset of video images in the additional dataset. Note that each video image in the subset of video images has a low-confidence level being either a tool-absent image or tool-present image. The process next provides true tool-present or tool-absent labels to the subset of video images. The process subsequently updates the trained tool detection model using the combined initial training dataset and the labeled subset of video images.

BRIEF DESCRIPTION OF THE DRAWINGS

The structure and operation of the present disclosure will be understood from a review of the following detailed description and the accompanying drawings in which like reference numerals refer to like parts and in which:

FIG. 6A illustrates an exemplary scenario of detecting an unsafe tool-use event by comparing an exemplary control signal of the energy tool including an activation pulse and an exemplary tool presence/absence signal generated by the disclosed tool presence/absence detection model in accordance with some embodiments described herein.

FIG. 6B illustrates an exemplary scenario of detecting another unsafe tool-use event by comparing an exemplary control signal of the energy tool including an activation pulse and an exemplary tool presence/absence signal generated by the disclosed tool presence/absence detection model in accordance with some embodiments described herein.

FIG. 6C illustrates an exemplary scenario of determining that the tool is safe to use by comparing an exemplary control signal of the energy tool including an activation pulse and an exemplary tool presence/absence signal generated by the disclosed tool presence/absence detection model in accordance with some embodiments described herein.

FIG. 6D illustrates another exemplary scenario of determining that the tool is safe to use by comparing an exemplary control signal of the energy tool including an activation pulse and an exemplary tool presence/absence signal generated by the disclosed tool presence/absence detection model in accordance with some embodiments described herein.

DETAILED DESCRIPTION

Figure 1:
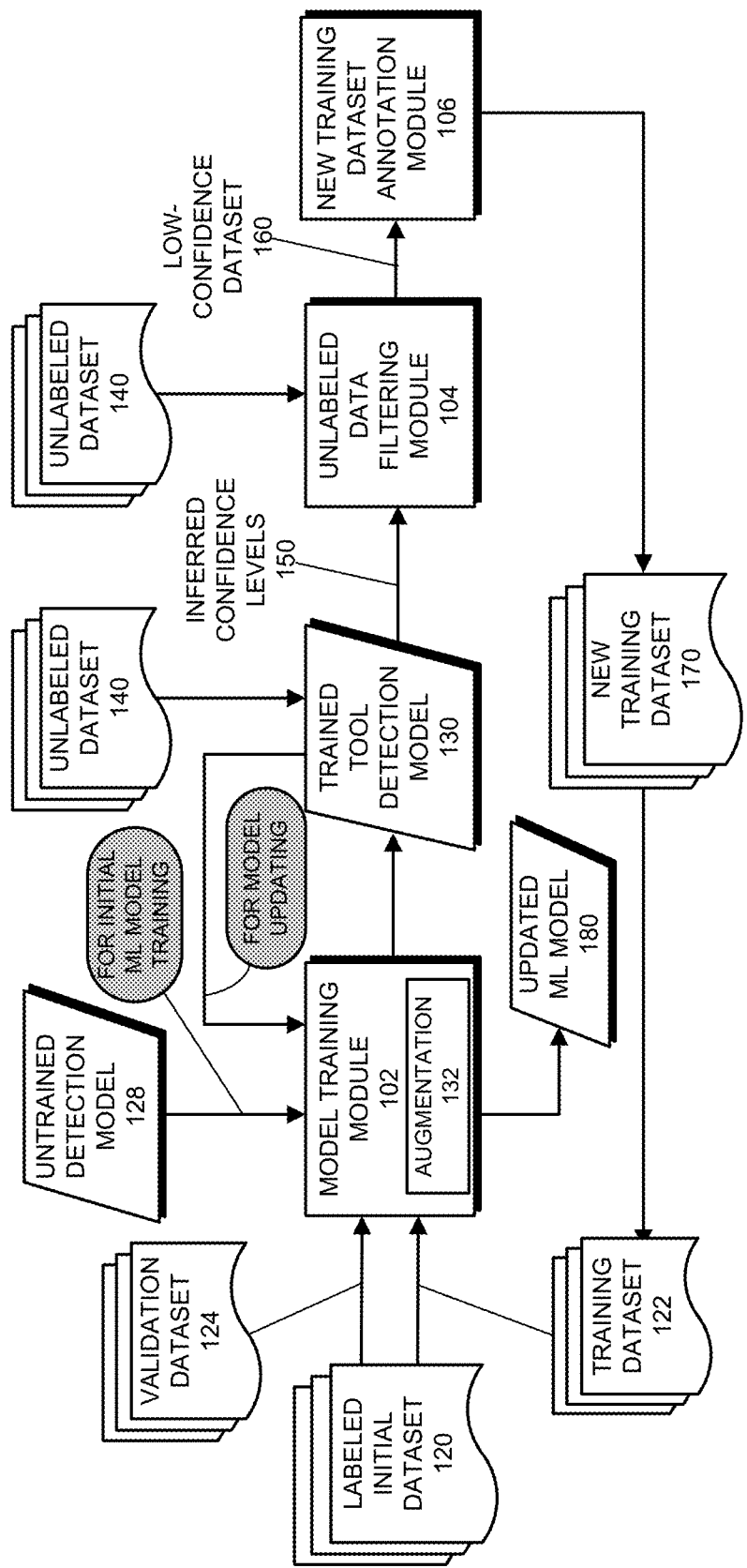
FIG. 1 shows a block diagram of an exemplary machine-learning (ML) model-training system for generating an energy tool presence/absence detection model through active learning in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Terminology

Throughout this patent disclosure, the terms "tool presence/absence detection model," "tool presence/absence detector" "tool detection model," "tool detector," "ML tool-detection model," and "ML tool detector" are used interchangeably to mean a deep-learning model constructed to predict whether a surgical tool, such as an energy tool is present or absent in a given surgical video frame and provide a confidence score to each prediction.

Overview

Embodiments described herein provide various techniques and systems for building machine-learning (ML)/deep-learning (DL) surgical tool detection models for processing surgical videos and predicting whether a surgical tool is present or absent in each video frame of a surgical video. In particular, the ML surgical tool detection models described in this disclosure include an energy tool presence/absence detection model which is trained and used to process a real-time surgical video of a laparoscopic or robotic surgery that uses an energy tool to cut and cauterize/seal tissues, and generate a real-time prediction for each video frame regarding whether the energy tool is present or absent in each video frame.

In various embodiments, the disclosed energy tool presence/absence detection model is built to detect multiple models and versions of a given type of the energy tool instead of a particular model or version of the given type of the energy tool. In some embodiments, a disclosed energy tool presence/absence detection model is built for various models and versions of an ultrasonic energy tool by one manufacturer, such as Harmonic™ scalpels by Ethicon™. However, a separate energy tool presence/absence detection model may be built for various models and versions of an ultrasonic energy tool by another manufacturer, such as Sonicision™ scalpels by Covidien™. Another disclosed energy tool presence/absence detection model can be built for various models and versions of a bipolar energy tool by one manufacturer, such as Enseal™ tissue sealers by Ethicon™. However, a separate energy tool presence/absence detection model may be built for various models and versions of a bipolar energy tool by another manufacturer, such as a Ligasure™ tissue sealers by Covidien™. The disclosed energy tool presence/absence detection model is further integrated with an energy-tool unsafe-use detection process to detect unsafe events associated with the energy tool usage during a surgery and to prevent injuries from the energy tool.

In various embodiments, the disclosed ML surgical tool detection model building techniques and systems can build a robust surgical tool detection model by first obtaining an initially trained tool detection model based on an initial training dataset, wherein the initial training dataset can include collected images of the surgical tool in different types and models, instead of just a particular type/model of the energy tool. This will allow building an initially trained tool detection model that can cover all types and models of the energy tool that are potentially in use everywhere. To increase training data diversity to cover more real-world scenarios, multiple data augmentation techniques including random color distortion and geometrical transformation can be carefully applied to the initial training dataset, while keeping the original labels of the images. The extended training dataset including both the initial training dataset and the augmented versions of the initial training images can be used to train an initial ML tool detection model and obtain the initially trained tool detection model.

The disclosed ML surgical tool detection model building techniques and systems also include mechanisms to update or further train the initially trained tool detection model based on additional training images related to the energy tool and energy tool usage. In some embodiments, the disclosed ML surgical tool detection model building techniques and systems update the initially trained tool detection model through the active learning, which can involve a training loop. This includes using the initially trained tool detection model to separate the additional training images into high-confidence-level images that are similar to images in the initial training dataset; and low-confidence-level images that are significantly different from images in the initial training dataset. The identified low-confidence-level images are then annotated by skilled annotators. Next, the disclosed ML surgical tool detection model building techniques and systems trains/updates the initially trained tool detection model using the labeled low-confidence-level images to update.

The updated surgical tool detection model can have improved accuracy and precision than the initially trained tool detection model, and can also detect more diverse and more complex surgical scenarios related to the surgical tool than the initially trained tool detection model.

Using the disclosed surgical tool detection model updating techniques, the initially trained tool detection model is updated on a significantly smaller but information-rich set of additional training images, which makes the model training/updating process much more efficient than using both high-confidence-level images and low-confidence-level images. Moreover, the convergence time during the model optimization is greatly reduced comparing with a training process without using active learning when the same validation dataset is used. Note that the disclosed ML surgical tool detection model building techniques and systems can be used not only to build energy tool presence/absence detection models, but also to build surgical tool detection models for surgical tools other than energy tools.

Building a Surgical Tool Presence/Absence Detection Model Through Active Learning Surgical videos including both laparoscopic surgery videos and robotic surgery videos captured during minimally invasive surgeries can help to improve both the efficiency and the quality of the surgeries by providing real-time visual feedback. Object detection models and techniques can leverage this visual feedback by extracting and analyzing information from a surgical video, such as detecting which surgical tools are used to enable various clinical use cases. In this disclosure, a deep-learning-based model and technique for performing frame-by-frame processing of a surgical video to detect an energy device (e.g., a Harmonic™ vessel sealer manufactured by Ethicon™) in the surgical video is disclosed.

In some embodiments, to train the disclosed deep-learning energy tool detection model, an initial training dataset of surgical images (e.g., —8000 images) related to the energy tool use are collected in the data collection phase. In some embodiments, these surgical images are collected from gastric bypass and sleeve gastrectomy procedures. The training images can be labeled by a number of resident surgeons who are highly skilled in the given surgical procedures and using the energy tool. To ensure the quality of labeled training data, annotation guideline and discussion along with a quality assurance procedure are developed. Moreover, a level of agreement around or above 90% across the number of annotators is consistently maintained.

To increase training data diversity to cover more real-world scenarios, multiple data augmentation techniques including random color distortion and geometrical transformation can be carefully applied to the initial training data set, while keeping the original labels of the images. The extended training dataset including both the initial training dataset and the augmented versions of the initial training images can be used to train an initial ML tool detection model. The initial ML tool detection model is then embedded within a training-validation loop equipped with an active learning pipeline to identify an additional training dataset of low confidence-level images. This additional training dataset (~e.g., ~2000-3000 images) can be subsequently labeled by the same team of annotators using the same annotation procedure and guideline, and the labeled additional training images are subsequently used to update the initial ML tool detection model.

By incorporating active learning into the disclosed ML tool detection model training procedure, the following improvements over conventional model training schemes have been achieved: (1) a significantly smaller number of training images is annotated; (2) additional training images that are significantly different from the initial training dataset can be identified from a large unprocessed image set and then used to updated the initially trained model; and (3) the convergence time during the model optimization is greatly reduced comparing with a training process without using active learning when the same validation dataset is used. Using the trained ML tool detection model obtained through the disclosed model training procedure, the following optimal F1-score, recall and precision across the validation dataset were obtained as 99.19%, 99.75% and 99.87%, respectively. A separate test dataset was also independently prepared which demonstrated best F1-score, recall and precision of 95.89%, 95.50%, 96.31%, respectively, while the datasets cover various surgical procedures.

FIG. 1 shows a block diagram of an exemplary machine-learning (ML) energy-tool-detection model building system 100 (or "ML model-building system 100" hereinafter) for generating an energy tool presence/absence detection model through active learning in accordance with some embodiments described herein. As can be seen in FIG. 1, ML model-building system 100 includes a model training module 102, a trained tool presence/absence detection model (or "trained tool detection model") 130, an unlabeled data-filtering module 104, and a new training dataset annotation module 106 which are coupled in a loop in the illustrated order. While a Harmonic™ scalpel/vessel sealer made by Ethicon™ is used as the main example of the energy tool described in conjunction with the disclosed ML model-building system 100 of FIG. 1, ML model-building system 100 can be used to train and update a tool presence/absence detection model for any model/type of a surgical tool/instrument that is used to simultaneously cut and cauterize/seal tissues during a surgery, and hence the energy tool described in this patent disclosure is not limited to Harmonic™ scalpels or a particular model/type of the energy tool.

To train an untrained energy-tool presence/absence detection model 128 (or "untrained detection model 128"), an initial dataset including a large number of unlabeled endoscope images extracted from a collection of surgical videos recorded during surgical procedures involving the energy tool is first collected. Note that the collection of surgical videos can be collected from various surgical procedures, including but are not limited to gastric bypass and sleeve gastrectomy. A large number of training images are needed partially because high quality data annotation requires multiple data annotators to be consistent and largely agree on many different scenarios. In some embodiments, the diversity of the data sources in the initial dataset is controlled by the number of different doctors and different hospital involved as well as different surgical procedures. Note that the initial dataset can include collected images of different types and models of the energy tool, instead of just a particular type and model of the energy tool. This will allow for building an initially trained tool detection model that can cover all types and models of the energy tool that are potentially in use around the world. For example, for Harmonic vessel sealers, the initial dataset should include the surgical image data of at least of the following tool types: (1) Harmonic Ace; (2) Harmonic Ace+; (3) Harmonic Ace+7; (4) Harmonic HD 1000i; and (5) Harmonic HD 1100, among others. The different types of the energy tool can also include both ultrasonic tools and bipolar tools.

In some embodiments, ~50% of the collected images in the initial dataset are tool-absent images (or "the first class"

images) used for detecting instances when the energy tool is not visible in a given endoscope image; while the other ~50% are tool-present images (or "the second class" images) used for detecting instances when the energy tool is visible in a given endoscope image. In some particular example, a total of 8000 raw surgical images for energy tool presence/absence detections are collected, of which 4000 images are the tool-absent/first class images while the other 4000 images are the tool-present/second class images. In other embodiments however, the ratio of the first class images and the second class images in the initial dataset can be different from 1:1. For example, another construction of the initial dataset can have ~40% of the first class images and ~60% of the second class images; while yet another construction of the initial dataset can have ~60% of the first class images and ~40% of the second class images.

In some embodiments, each class of the training images may be further broken down into a number of common subclasses/cases. For example, considering that each cutting/sealing sequence (or an "activation sequence") by a Harmonic sealer on a tissue can typically comprise multiple shorter firing events (i.e., multiple activation events) with inactive gaps between the multiple activation events, the tool-absent/first class images may further include the following five subclasses: (A1) only anatomy, no tool images; (A2) outside activation-sequence images; (A3) in-between activation events images; (A4) during activation event images; and (A5) other surgical-tool keypoint images. In one real-world example, a dataset of 4086 tool-absent images has the following breakdown corresponding to above five subclasses A1-A5: (A1) 100 images; (A2) 1658 images; (A3) 2065 images; (A4) 24 images; and (A5) 239 fdimages. Similarly, the tool-present/second class images may further include the following three subclasses: (P1) during activation event images; (P2) between activation events images; (P3) the energy-tool keypoint images. In the real-world example, a dataset of 3996 tool-present images has the following breakdown corresponding to above three subclasses P1-P3: (P1) 623 images; (P2) 3318 images; (P3) 55 images.

After the above-described data collection process to obtain the initial dataset, the initial dataset is labeled by a number of resident surgeons (e.g., between 2-5 surgeons) who are highly skilled with the energy tool and the surgical procedure depicted in the training images. To ensure the quality of labeled data, annotation guideline and discussion along with fa quality assurance procedure should be developed. For example, the quality assurance procedure can include performing statistical analysis to uncover anomalies and to identify similarities among the group of annotators in order to increase the level of full agreement among the annotators. As a general requirement, a level of full agreement around 90% across all annotators should be consistently maintained. For those training images that involve disagreements among annotators, additional review and discussion are used to determine the cause of the disagreements, and labels with consensus are eventually obtained. In practice, it has been observed that annotators generally have very high agreement on both true tool-present cases and true tool-absent cases. However, some disagreement can occur on a few true tool-absent cases (such as cases where the tool is maneuvering around the edge of an image frame), while disagreement rarely occurs on most or all true tool-present cases.

After data annotation on the initial dataset, the labeled initial dataset 120 shown in FIG. 1 is obtained. Next, ML model-building system 100 uses model training module 102 and the labeled initial dataset 120 to train an untrained tool presence/absence detection model 128 (or "untrained detection model 128"), and output a trained presence/absence detection model 130. In various embodiments, untrained detection model 128 can be implemented using various convolutional neural network (CNN/ConvNet) architectures. For example, untrained detection model 128 can be implemented with a residual neural network (ResNet). In a particular embodiment, untrained detection model 128 is implemented with ResNet18 with all layers in the network unfrozen.

As can be seen in FIG. 1, during the model training, labeled initial dataset 120 is divided into a training dataset 122 and a validation dataset 124. As one practical example, 8000 images in the labeled initial dataset 120 is divided into the training dataset including 80% of the total images, and the validation dataset with the rest of the 20% of the total images. In addition, an independent test dataset equal to the size of validation dataset 124 can also be prepared. In some embodiments, model training module 102 is configured to train an untrained tool presence/absence detection model 128 through a number of N epochs (e.g., N=200) based on the training dataset 122. At the end of each epoch, model training module 102 calculates the recall, precision, the F1-score, and accuracy values over the validation set 124, and stores the set of updated model parameters. At the end of N epochs, the set of stored model parameters corresponding to a given epoch that generates the best performance metric, e.g., the highest recall value is chosen as the trained presence/absence detection model 130. A person skilled in the art will appreciate that depending on which best metric value of the four performance metrics (i.e., recall, precision, the F1-score, and accuracy) is used, a slightly different trained model 130 can be obtained, each having its own strength and weakness. Note that from the clinical point of view, a trained model 130 having the highest recall value may be preferred due to the fact that the version of the trained model 130 can provide the best performance for capturing the most number of tool-absent (i.e., tool off-screen) events.

As can be seen in FIG. 1, model training module 102 also includes a data augmentation submodule 132. In various embodiments, data augmentation submodule 132 is configured to perform a number of image augmentation operations on a given image in the labeled initial dataset 120 to generate a number of transformed/augmented images of the initial image. Note that regardless the types of image augmentations are used on a given initial image, the resulting augmented images should have the same present/absent label as the given initial image. In various embodiments, the image augmentation operations that can be performed by data augmentation submodule 132 can include an image scaling function. Specifically, the image scaling function is configured to multiply the original height and width of a given initial image by one random number (but does not change the aspect). This random number can be chosen from a range provided by the data scientist, e.g., a range that is between 0 and 1. Note that this image augmentation function can be seen as a zoom-in function by a random amount. The image augmentation operations can also include an aspect ratio augmentation. Specifically, the ratio function is configured to multiply the original aspect ratio of the initial image by a random number. This random number can be chosen from a range provided by the user, e.g., a range that is between 0 and infinity. The image augmentation operations can also include a cropping/resizing function. Specifically, the cropping/resizing function is configured to first randomly crop out a portion of the initial image and subsequently resize the cropped image to a predetermined size, e.g., (244, 244).

Note that data augmentation submodule 132 can also be configured to perform the following image augmentation functions on a given initial image: (1) rotating the image, either clockwise or counterclockwise; (2) flipping the image, either with respect to the horizontal axis or the vertical axis; (3) changing the image brightness; (4) changing the image color tunes; (5) changing the image resolution; among others. Note that although data augmentation submodule 132 can generate the various types of augmented images artificially based on the initial dataset 120, the augmented images are generally used to mimic real world scenarios that can happen but are not necessarily included in the initial dataset 120. For example, suppose that the common tool positions are on the right side of the image frames with the tool tip pointing to the left due to most of the surgeons holding the tool with the right hand, the surgical tool images from a left-handed surgeon may appear on the left side of the image frames with the tool tip point to the right. By performing a left-right imaging flipping operation on the initial images, the above scenario can be simulated. As another example, the qualities of endoscope videos from different hospitals around the world are vastly different, leading to capturing videos of various color ranges. This video color variation can be simulated by performing color manipulations in the image augmentation process. Furthermore, the surgical image rotations caused by the axis of the endoscope constantly rotating inside the abdomen of a patient during the surgery can be simulated by a random rotation of the images during the image augmentation process.

Note that through the N epochs of model training, a given image in the labeled initial dataset 120 may be transformed differently using different image augmentation functions in different epochs. In some embodiments, after training tool detection model 128 using the original labeled initial dataset 120 in the first epoch of N epochs of model training, model training module 102 is configured to transform a randomly-selected subset of the labeled initial dataset 120 into corresponding augmented images using data augmentation submodule 132 at the beginning of each subsequent epoch of model training. Specifically, to transform a given image in the randomly-selected subset, data augmentation submodule 132 can randomly apply one of the available image augmentation functions to the given image. After the training dataset transformation, the original labeled initial dataset 120 becomes a modified training dataset comprising both the augmented and labeled images and original labeled images from labeled initial dataset 120. Next, model training module 102 is configured to train tool detection model 128 using the modified training dataset generated for each subsequent epoch. As such, instead of using the same labeled initial dataset 120 for all training epochs, the above-described training technique adds a new set of data diversities into the training dataset for each epoch of model training. Consequently, the trained detection model 130 at the end of N epochs is able to identify and correctly classify significantly more tool present/absent situations that can arise in surgical procedures than the trained detection model 130 without adding the augmented images into the training process.

Referring back to FIG. 1, note that after generating trained tool detection model 130, ML model-building system 100 then applies trained tool detection model 130 to an unlabeled image dataset 140. Note that unlabeled dataset 140 may be obtained at the same time when the labeled initial dataset 120 was collected or unlabeled image dataset 140 may be obtained separately before or after the labeled initial dataset 120 was collected. Because image data annotation work is highly labor intensive, it is not practical to manually annotate all of the collected image data. However, after tool detection model 130 is trained based on a reasonably-sized initial dataset 120, unlabeled image dataset 140 can now be processed and used to further train and improve trained tool detection model 130 through a process of Active Learning. In some embodiments, unlabeled image dataset 140 is collected after the labeled initial dataset 120 was collected for a new model or a new type of the energy tool, e.g., a new type of Harmonic™ scalpel that has just become commercially available but has not been built into the trained tool detection model 130.

Note that the general concept of Active Learning is that, for the best training data annotation efficiency and effectiveness, data annotation resources and priority should be given to those date/images containing the most information, i.e., those scenarios unfamiliar to the trained model, referred to as "low confidence" data to the trained model. In other words, for those scenarios which are already built into the trained model, it is unnecessary and inefficient to collect and label the same types of data and update the model with such data, because they are "high confidence" data to the trained model. Furthermore, labeling these "high confidence" data and including them in the training process could also lead to an overfitting problem. Without processing, unlabeled image dataset 140 can contain a large amount of such high confidence images to trained tool detection model 130. Hence, instead of manually labeling and retraining the model using these high confidence images, these high confidence images should be removed from unlabeled image dataset 140. In contrast, those low confidence data in unlabeled dataset 140 should be identified and labeled as new training data.

Using the concept of active learning, trained tool detection model 130 and unlabeled data-filtering module 104 are used collectively to select a subset of unlabeled image dataset 140 that has the most information unfamiliar to trained tool detection model 130. More specifically, trained tool detection model 130 processes unlabeled image dataset 140 and outputs a set of confidence levels 150 for the set of images in unlabeled image dataset 140, wherein each confident level in the set of confidence levels 150 is between (0, 1). For a given image in unlabeled image dataset 140, if the corresponding confidence level in the set of confidence levels 150 is very close to 1, it indicates that trained tool detection model 130 is highly confident that the target energy tool is detected in the given image (i.e., detecting a tool-present scenario). On the other hand, if the output confidence level for the given image very close to 0, it indicates that trained tool detection model 130 is highly confident that the target energy tool is absent in the given image (detecting a tool-absent scenario). However, if the output confidence level for the given image is neither close to 1 nor to 0 but lies somewhere between (0, 1), e.g., 0.6 or 0.7, it means that trained tool detection model 130 is not sufficiently confident on either a tool-presence or a tool-absence decision for the given image. Unlabeled data-filtering module 104 can then filter unlabeled image dataset 140 and outputs a low-confidence dataset 160 that includes only those images having low-confidence levels. Such images are the above-described low confidence data of the highest interest, which can now be passed to the annotators to be labeled. As such, Active Learning implemented in ML model building system 100 only selects those low-confidence images in unlabeled image dataset 140, instead of labeling the entire unlabeled image dataset 140.

Note that by using active learning in the process of training the tool detection model, the number of epochs that is needed to converge to the optimal model performance can be significantly reduced (given the same validation dataset is used). In an exemplary training process, it was observed that before using active learning, 184 epochs were needed to get the optimal recall score of the model. However, after using active learning, only 6 epochs were used to obtain the same recall score of the model. This improvement in model training performance is due to the fact that active learning can refine the training dataset by enriching the information in the training dataset and as a result, the model optimizer converges more quickly to the best answer on the same validation dataset.

Figure 2:
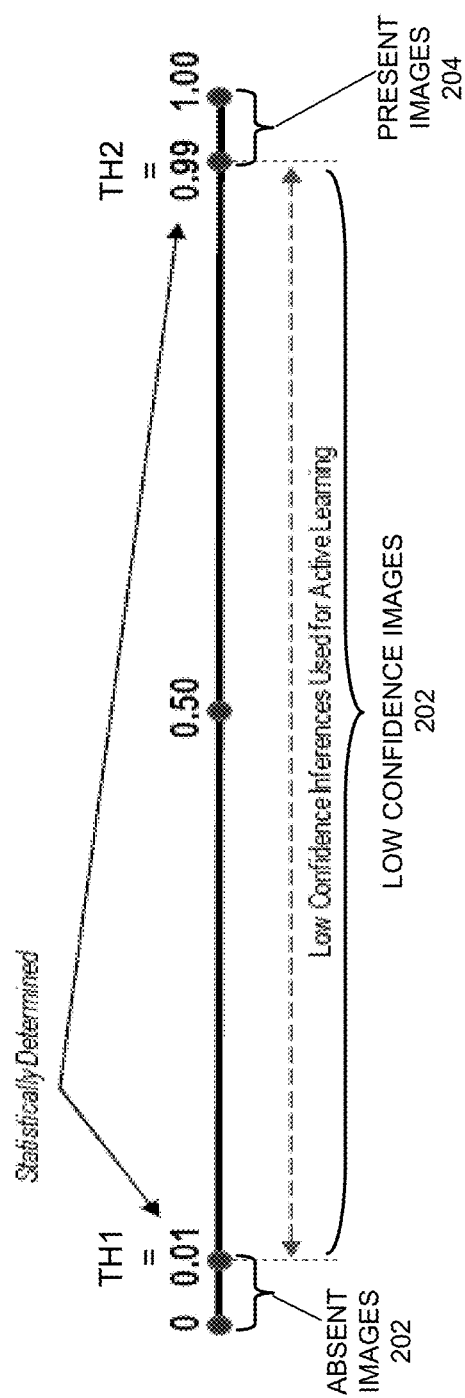
FIG. 2 shows an exemplary data-filter configuration with two thresholds $TH_1$ and $TH_2$ defining the boundaries between high confidence data and low confidence data in accordance with some embodiments described herein.

To identify the low confidence data and to filter out the high confidence data, unlabeled data-filtering module 104 is configured with two thresholds $TH_1$ and $TH_2$. Generally speaking, threshold $TH_1$ should be set to be very close to 0 to separate high-confidence absent images and low-confidence absent images. In contrast, threshold $TH_2$ should be set to be very close to 1 to separate high-confidence present images and low-confidence present images. Hence, the range between $TH_1$ and $TH_2$ corresponds to low confidence levels. FIG. 2 shows an exemplary data-filter configuration with two thresholds $TH_1$ and $TH_2$ setting the boundaries between high confidence data and low confidence data in accordance with some embodiments described herein. In the example show, $TH_1$ is set to 0.01 which means inferred confidence levels near or below 0.01 for images in unlabeled image dataset 140 is considered as a high-confidence tool-absent image 202. Moreover, $TH_2$ is set to 0.99 which means inferred confidence levels near or above 0.99 for images in unlabeled image dataset 140 are considered as high-confidence tool-present images 204. As such, the range (0.01, 0.99) corresponds to the low confidence levels. As a result, those images that have inferred confidence levels fall between the range (0.01, 0.99), e.g., 0.5, are identified as the low confidence images 206 which are selected and included in the low-confidence dataset 160 as the output of unlabeled-data filtering module 104.

Note that the two threshold values 0.01, 0.99 are just example values that can provide sufficiently good filtering results. Generally speaking, the values of $TH_1$ and $TH_2$ are statistical determined. For example, $TH_1$ and $TH_2$ can be determined based on the determined recall score of trained tool detection model 130. In this regards, for instance, the two thresholds $TH_1$ and $TH_2$ can be determined by analyzing the result of the validation dataset. More specifically, we can first gather the confidence levels of those samples in the of the validation dataset that are incorrectly inferred by the trained tool detection model 130, and subsequently determine the range of gathered confidence levels that contains false negative and false positives. The two thresholds, TH1 and TH2 can be automatically obtained from the two boundaries of the determined range. Those unlabeled image dataset 140 identified in low-confidence dataset 160 can then be annotated/labeled by new training dataset annotation module 106, which generally includes the same manual-annotation procedures by the skilled annotators as described above.

As a continuation of the practical example that started with 8000 raw surgical images for the Harmonic-sealer tool presence/absence detection, additional 12,000 raw surgical images for the Harmonic-sealer tool were collected. Instead of manual annotating these 12,000 images, they are passed through the disclosed ML model-building system 100, and only ~2700 (~23%) of the 12,000 images were identified as low confidence images with new information, and subsequent labeled. In other words, by using Active Learning and the disclosed ML model-building system 100, the additional annotation effort on the 12,000 images can be greatly reduced.

After low-confidence dataset 160 within unlabeled image dataset 140 are annotated/labeled, a new training dataset 170 are obtained. Using the above example, new training dataset 170 would include ~2700 new training image. In the disclosed ML model-building system 100, new training dataset 170 is combined with initial training dataset 122 to obtain a combined training dataset that has a greater size and more diverse and complex than initial training dataset 122. In some embodiments, the combined training dataset is used to update trained tool detection model 130 in the model training loop. This is shown in FIG. 1 where model training module 102 receives trained tool detection model 130 and the combined training dataset 122 and 170 as inputs and an updated tool detection model 180 as output. Note that updating trained tool detection model 130 means that the model will be trained from its present state. In other words, trained tool detection model 130 is not re-trained from the scratch but further trained from the present state of the model. Note that while the training dataset has grown in size and diversity, validation dataset 124 can remain the same so that a fair comparison can be made between the trained tool detection model 130 without the active learning and the updated tool detection model 130 based on the combined training dataset.

Note that one practical reason of updating trained tool detection model 130 is to obtain an updated version of the tool detection model for a new version/type of the energy tool that has not been built into the trained tool detection model 130. As mentioned above, to update tool detection model 130 for a new version/type of the energy tool, unlabeled image dataset 140 can be generated for the new version/type of the energy tool, e.g., a new type of Harmonic™ sealer that has just become commercially available. Generally speaking, the new version/type of the energy tool may differ from the existing versions/types of the energy tool that have been built into the trained tool detection model 130 to some degree, e.g., in terms of changes in colors, in terms of changes in geometries, in terms of changes in printed text, or in terms of missing or additions certain mechanical features/parts. However, the new version/type of the energy tool is also largely the same in overall appearance as the existing versions/types of the energy tool that have been built into the trained tool detection model 130. As such, it is unnecessary to re-train the trained tool detection model 130 on the entire unlabeled image dataset 140 generated for the new version/type of the energy tool. Using the disclosed ML model-building system 100 with an active learning loop, a subset of low-confidence images 160 within the unlabeled image dataset 140 that contains the useful information of the new version/type of the energy tool but that has not been built into the trained tool detection model 130 (e.g., changes in colors, geometries, printed text, and/or missing or additions certain mechanical features/parts) can be identified and used to update the trained tool detection model 130. However, those images in the unlabeled image dataset 140 that can be inferred by the trained tool detection model 130 with high confidences are identified and removed.

Figure 3:
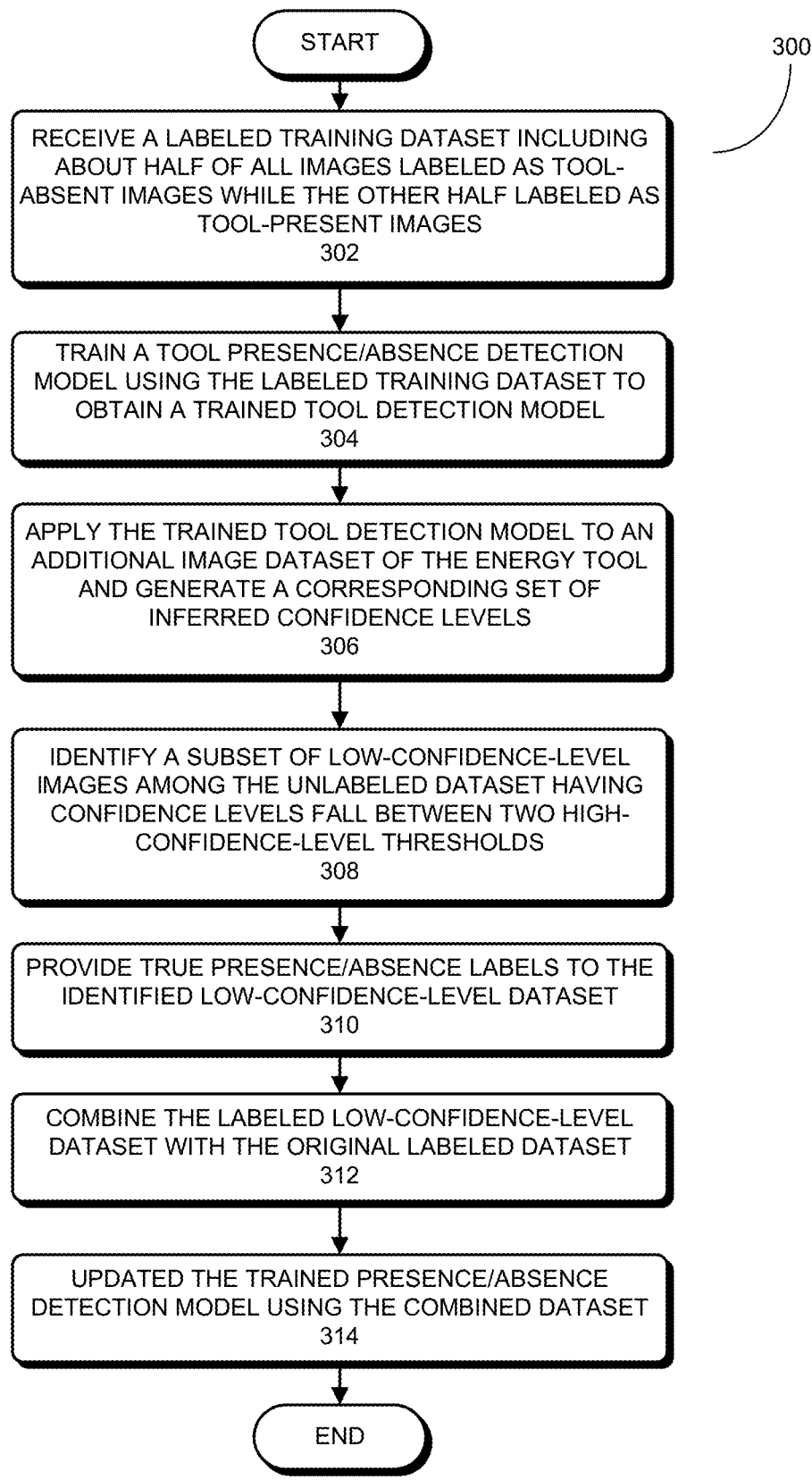
FIG. 3 presents a flowchart illustrating an exemplary process for generating an energy tool presence/absence detection model through active learning in accordance with some embodiments described herein.

FIG. 3 presents a flowchart illustrating an exemplary process for generating an energy tool presence/absence detection model through active learning in accordance with some embodiments described herein. In one or more embodiments, one or more of the steps in FIG. 3 may be omitted, repeated, and/or performed in a different order.

Accordingly, the specific arrangement of steps shown in FIG. 3 should not be construed as limiting the scope of the technique.

Process 300 may begin by receiving a labeled training dataset including about half of all training images labeled as tool-absent images while the other half of the training images are labeled as tool-present images (step 302). Note that to obtain the labeled training dataset, an initial dataset including a large number of unlabeled endoscope images recorded during the surgical tasks involving the energy tool has to be collected, and ~50% of the collected images are tool-absent images used for detecting instances when the energy tool is not visible in a given endoscope image; while the other ~50% are tool-present images used for detecting instances when the energy tool is visible in a given endoscope image. However, as described above, the breakdown between the tool-absent images and the tool-present images in the initial training dataset can be different from ~50% for each type of images, for example, the breakdown can be 60%/40% or 40%/60% for the two types of labled images. The labeled training dataset is subsequently generated through a manual annotation procedure by a group of highly skilled surgeons with the energy tool and the surgical procedure depicted in the training images.

Next, process 300 trains a tool presence/absence detection model using the labeled training dataset to obtain a trained tool presence/absence detection model (step 304). In some embodiments, when training the tool presence/absence detection model over a number of epochs based on the labeled training dataset, process 300 can apply data augmentations such as random color distorting and geometrical transformation on a subset of the training dataset in different epochs to increase the diversity of the training data in a realistic manner while not altering the labels of the augmented images from the original labeled images.

After generating the trained tool presence/absence detection model, process 300 then applies the trained tool detection model to an additional image dataset of the energy tool and generates a corresponding set of inferred confidence levels for the unlabeled image dataset (step 306). Next, process 300 identifies a subset of low-confidence-level images among the additional image dataset that has inferred confidence levels fall between two high-confidence-level thresholds corresponding to tool-absent prediction and tool-present prediction, respectively (step 308). Note that one of the two high-confidence-level thresholds is close to 0 (e.g., 0.1) indicating a high-confidence of detecting that the tool is absent in an image wherein the other confidence-level threshold is close to 1 (e.g., 0.99) indicating a high-confidence of detecting that the tool is present in an image. In various embodiments, the values of the two high-confidence-level thresholds are statistical determined. Process 300 then provides true presence/absence labels to the identified low-confidence-level dataset through a manual annotation procedure (step 310). Process 300 next combines the labeled slow-confidence-level dataset with the original labeled training dataset to generate an updated training dataset (step 312). Process 300 subsequently updates the trained presence/absence detection model using the updated training dataset (step 314).

Enemy Tool Real-Time Safety Monitoring Using Tool Present/Absent Detector

Figure 4:
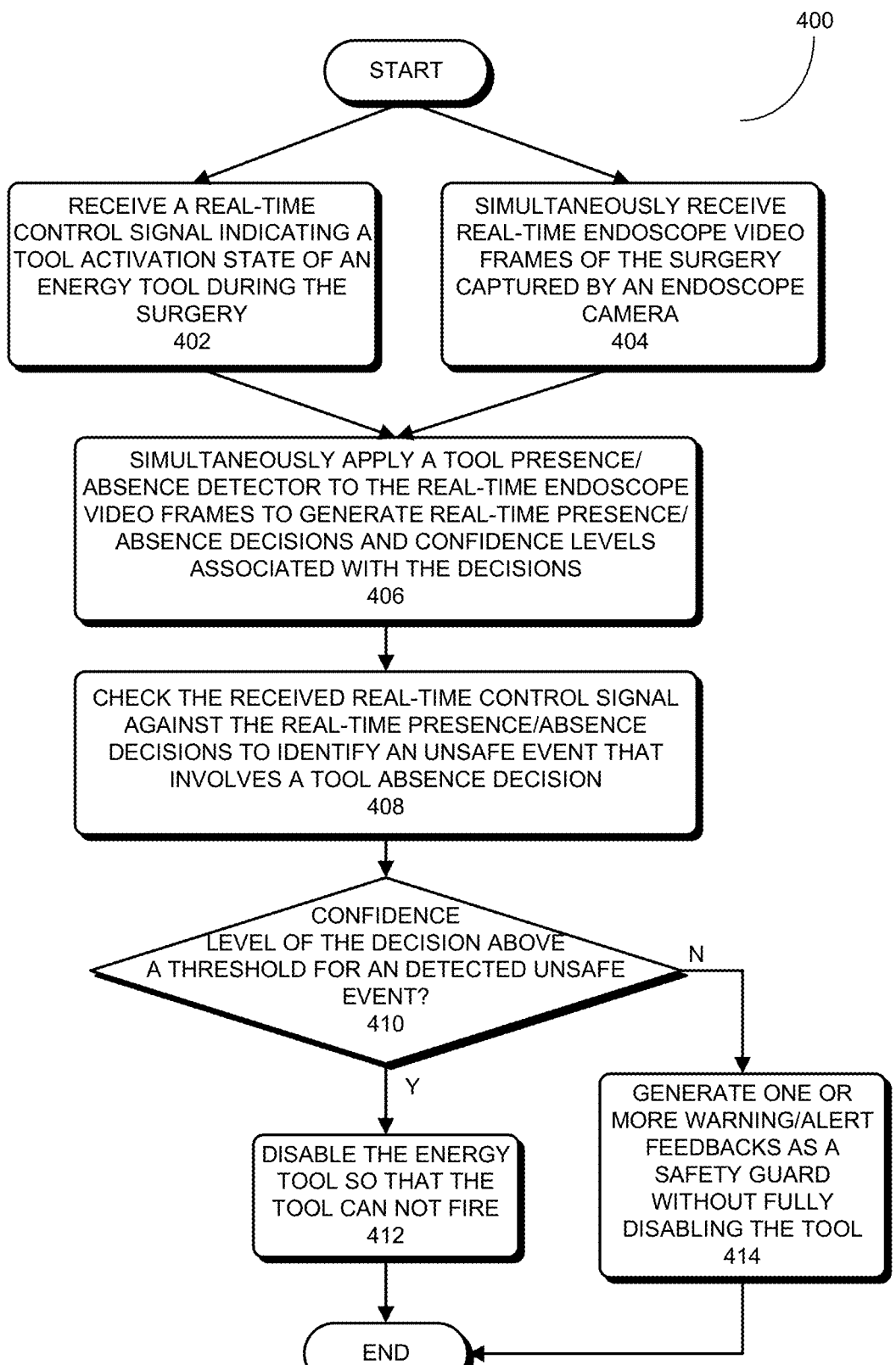
FIG. 4 presents a flowchart illustrating an exemplary process for preventing injuries from an energy tool used for cutting/sealing tissues during a laparoscopic or robotic surgery in accordance with some embodiments described herein.

FIG. 4 presents a flowchart illustrating an exemplary process 400 for preventing injuries from an energy tool used for cutting/sealing tissues during a laparoscopic or robotic surgery in accordance with some embodiments described herein. In one or more embodiments, one or more of the steps in FIG. 4 may be omitted, repeated, and/or performed in a different order. Accordingly, the specific arrangement of steps shown in FIG. 4 should not be construed as limiting the scope of the technique.

Process 400 may begin by receiving a real-time control signal indicating a tool activation state of an energy tool during a surgery (step 402). In some embodiments, the real-time control signal is received from a tool controller. For example, in the case of a harmonic ultrasonic sealer, the control signal is generated by a Ethicon™ generator such as Gen11™. Note that however, each activation decision during the surgery is made by the surgeon and initiated by pulling on a handle on the energy tool or pressing a button on the tool. The surgery action then triggers the generator to begin generating an activation pulse which is then transmitted to the tool and energizes the jaws of the tool. Note that in conventional systems, as long as the handle is not released or the activation button is not pressed again, the activation pulse continues to be generated and the energy tool remains activated. However, the activation pulse stops when the handle is released or the activation button is pressed again, thereby by disabling the energy tool. Note that at the end of the current activation session, the activation pulse data, including the starting and ending timestamp (or alternatively the duration of the pulse) and the power settings are logged by the generator. As a result, at the end of the surgery the generator logs a sequence of activation pulses, wherein each activation pulse corresponds to a single activation/firing event of the energy tool.

While receiving the real-time control signal, process 400 simultaneously receives real-time endoscope video frames of the surgery captured by an endoscope camera (step 404) and simultaneously applies the above-described energy tool presence/absence detector to the real-time endoscope video frames as the video frames are being received to generate a real-time tool presence/absence decision for each processed video frame as well as a confidence level associated with each presence/absence decision (step 406). In various embodiments, the tool presence/absence detector described herein is generated by the disclosed ML model-building system 100 in FIG. 1. In some embodiments, the presence/absence decision can include: (1) tool presence decision indicating the energy tool is present in the given video frame; and (2) a tool absence decision indicating the energy tool is absent in the given video frame. Note that each decision is also associated with a confidence level, and a low confidence level is generally not expected because the training data used to train the tool presence/absence detector covered potential edge cases that could appear in each image frame, such as a tool too close to the edge or an occluded tool. In contrast, a high confidence level below the confidence level threshold TH1 for an absence decision generally means the tool is not visible in the given endoscope image; whereas a high confidence level above the confidence level threshold TH2 for a presence decision generally means the tool is fully visible in the given endoscope image.

Figure 5:
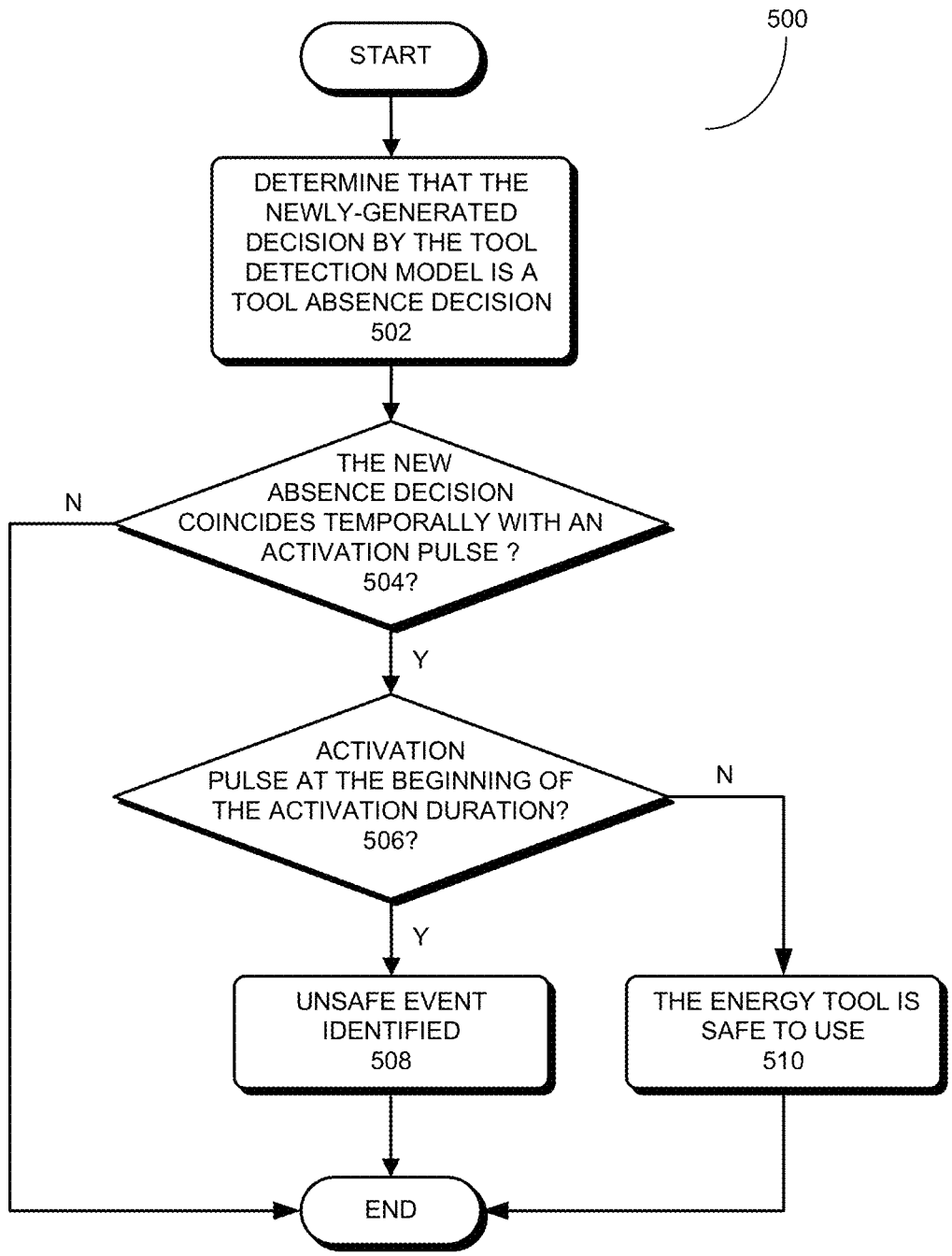
FIG. 5 presents a flowchart illustrating an exemplary process for making proper safe/unsafe determinations based on the received real-time control signal and the real-time presence/absence decisions from the tool presence/absence detector in accordance with some embodiments described herein.

Next, process 400 checks the received real-time control signal against the real-time presence/absence decisions to identify an unsafe event that involves a tool absence decision (step 408). Note that because the real-time presence/absence decisions are generated on a frame-by-frame basis, step 408 can also be performed on a frame-by-frame basis for each newly-generated presence/absence decision on an endoscope video image. FIG. 5 presents a flowchart illustrating an exemplary process 500 for making proper safe/unsafe determinations based on the received real-time control signal of the energy tool and the real-time presence/ absence decisions on the endoscope video images from the tool presence/absence detector in accordance with some embodiments described herein. In one or more embodiments, one or more of the steps in FIG. 5 may be omitted, repeated, and/or performed in a different order. Accordingly, the specific arrangement of steps shown in FIG. 5 should not be construed as limiting the scope of the technique.

Process 500 begins by determining that the newly-generated (i.e., current) decision by the tool presence/absence detection model is a tool absence decision (step 502). Process 500 next determines if the tool absence decision coincides temporally with an activation pulse in the real-time control signal (step 504). For example, process can determine that the new absence decision is generated inside an activation pulse of the real-time control signal when the real-time control signal is HIGH. If the new tool absence decision coincides with the activation pulse, process 500 further determines if the current activation pulse is at the beginning of the corresponding activation duration (step 506). In some embodiments, process 500 determines whether the current activation pulse is at the beginning of the current activation duration by computing a time period from when the current activation pulse first transitions to HIGH until the current time. Process 500 subsequently determines that the current activation pulse is at the beginning of the current activation duration if the computed time period is shorter than a predetermine time period based on an average activation duration of the energy tool during a surgical procedure.

As described above, the highly unsafe scenario that the real-time energy tool safety monitoring system is designed to avoid is when the energy tool is just beginning to fire but the tool is off screen (e.g., when both jaws of the energy tool are not in the video frame) and not visible to the user. Hence, if process 500 determines that the current activation pulse is at the beginning of its activation duration when the new tool absence decision is generated, process 500 identifies an unsafe event (step 508). FIG. 6A illustrates an exemplary scenario of detecting an unsafe tool-use event by comparing an exemplary control signal 602 of the energy tool including an activation pulse 604 and an exemplary tool presence/absence signal 606 generated by the disclosed tool presence/absence detection model in accordance with some embodiments described herein. As can be seen in FIG. 6A, tool presence/absence signal 606 is composed of both tool absence decisions which correspond to the LOW (~0) values of tool presence/absence signal 606; and tool presence decisions which correspond to the HIGH (~1) values of tool presence/absence signal 606. Moreover, activation pulse 604 in control signal 602 corresponds to the HIGH values in control signal 602. It can be observed that tool presence/absence signal 606 includes a sequence of tool absence decisions 608 that coincides/overlaps with activation pulse 604. Moreover, the time period 610 that the sequence of tool absence decisions 608 coincides/overlaps with activation pulse 604 is the beginning/early portion of the activation pulse 604 when the energy tool begins to fire. Hence, the exemplary scenario depicted in FIG. 6A represents an unsafe tool-use event that should be detected. This unsafe tool-use event can detected by checking any absence decision (e.g., absence decision 612) within absence decisions 608 against activation pulse 604, and detecting that the absence decision falls within the early activation time period 610 of activation pulse 604.

FIG. 6B illustrates an exemplary scenario of detecting another unsafe tool-use event by comparing an exemplary control signal 622 of the energy tool including an activation pulse 624 and an exemplary tool presence/absence signal 626 generated by the disclosed tool presence/absence detection model in accordance with some embodiments described herein. As can be seen in FIG. 6B, tool presence/absence signal 626 is composed of a short pulse of tool presence decision(s) 628 which corresponds to the HIGH (~1) values of tool presence/absence signal 626 which is then followed by a long period of tool absence decisions 630 which correspond to the LOW (~0) values of tool presence/absence signal 626. Note that even though quick tool presence decision(s) 628 were generated at the beginning of activation pulse 624, tool absence decisions 630 begin to be generated right after tool presence decision(s) 628 which coincide/overlap with activation pulse 624. Moreover, early portion of tool absence decisions 630 also coincides/overlaps with the beginning/early portion of the activation pulse 624 when the energy tool begins to fire. Hence, the exemplary scenario depicted in FIG. 6B also represents an unsafe tool-use event that should be detected. This unsafe tool-use event can detected by checking any absence decision (e.g., absence decision 650) within absence decisions 630 against activation pulse 624, and detecting that the absence decision falls within the early activation time period of activation pulse 624.

However, if process 500 determines that the current activation pulse is not at the beginning of the activation duration when the new tool-absence decision is generated, process 500 determines that the energy tool is safe to use (step 510). As described above, the tool absence decisions can occur toward the end of a given activation duration, or even in the middle of the activation duration when the endoscope camera has already moved away from the location of energy tool. However, because the energy tool itself most likely still remains in place, it is reasonable to assume that the energy tool has no safety concerns. FIG. 6C illustrates an exemplary scenario of determining that the tool is safe to use by comparing an exemplary control signal 632 of the energy tool including an activation pulse 634 and an exemplary tool presence/absence signal 636 generated by the disclosed tool presence/absence detection model in accordance with some embodiments described herein. As can be seen in FIG. 6C, tool presence/absence signal 636 is composed of both tool absence decisions which correspond to the LOW (~0) values of tool presence/absence signal 636; and tool presence decisions which correspond to the HIGH (~1) values of tool presence/absence signal 636. Moreover, activation pulse 634 in control signal 632 corresponds to the HIGH values in control signal 632. It can be observed that tool presence/absence signal 636 includes a sequence of tool presence decisions 638 that substantially coincides/overlaps with activation pulse 634. Also during the same time period of activation pulse 634, there is no tool absence decision generated. Hence, the exemplary scenario depicted in FIG. 6C represents a safe tool-use scenario.

FIG. 6D illustrates another scenario of determining that the tool is safe to use by comparing an exemplary control signal 642 of the energy tool including an activation pulse 644 and an exemplary tool presence/absence signal 646 generated by the disclosed tool presence/absence detection model in accordance with some embodiments described herein. As can be seen in FIG. 6D, tool presence/absence signal 646 is composed of both tool absence decisions which correspond to the LOW (~0) values of tool presence/absence signal 646; and tool presence decisions which correspond to the HIGH (~1) values of tool presence/absence signal 646. Moreover, activation pulse 644 in control signal 642 corresponds to the HIGH values in control signal 642. It can be observed that tool presence/absence signal 646 includes a sequence of tool absence decisions 648 that coincides/overlaps with activation pulse 644. However, the time period 660 that the sequence of tool absence decisions 648 coincides/overlaps with activation pulse 644 is toward the end of activation pulse 644. As described above, the exemplary scenario depicted in FIG. 6D also represents a safe tool-use scenario. This safe tool-use decision can be made by checking any absence decision within the sequence of absence decisions 648 against activation pulse 644, and detecting that no absence decision 648 falls within the early activation time period of activation pulse 644.

Returning to FIG. 4, if after checking the real-time control signal against the real-time presence/absence decisions, process 400 identifies the unsafe event that involves a newly-generated tool absence decision, process 400 next determines if the confidence level associated with the newly-generated tool absence decision is above a high confidence level threshold (step 410). Note that a high confidence level for a tool absence decision generally means the tool is completely missing in the given endoscope image. If so, process 400 immediately disables the energy tool so that the tool can not fire (step 412). However, if process 400 determines that the confidence level associated with the newly-generated tool absence decision is below the high confidence level threshold, process 400 can generate one or more warning/alert feedbacks as a safety guard without fully disabling the tool (step 414). The types of warning/alert feedbacks can include, but are not limited: (1) generating and displaying a visual alert/feedback on an endoscope monitor; (2) generating an audio alert through a console speaker; (3) generating a mechanical vibration through the energy tool; and (4) a mechanical/tactile feedback that delays the firing of the energy tool until the user takes a further action. For example, the mechanical/tactile feedback can be implemented as an interlock design that requires two-stop activation. More specifically, the first stop of the interlock design is used for generating the activation pulse and triggering the detection of an unsafe event. In this regard, the mechanical warning is provided to the user if the tool does not fire at the first stop, or the warning can be the fact that the energy tool does not fire at the first stop which is certainly noticed by the user. At the moment, the user can choose to inspect the endoscope video before taking another action, or alternatively the user may choose to proceed to fire the tool by applying extra force on the firing handle or button until the second stop of the interlock design is reached.

Note that the exemplary process 400 is designed to identify an unsafe event after each newly presence/absence decision is made based on a new video frame. However, this technique can be computationally-intensive and also susceptible to false positives. Realizing that the primary unsafe event is when the energy tool just begins to fire but the tool is missing from the endoscopic view, it is possible to modify process 400 to obtain more efficient process to detect such unsafe event. More specifically, when the real-time control signal indicates that the energy tool is idle, i.e., no activation pulse exists (e.g., when the signal is LOW), the modified process does not have to use the ML tool-detection model to detect whether the real-time endoscope images include the energy tool or not because the tool is inherently safe. However, the modified process continues to detect a new activation pulse in the control signal. When the beginning of a new activation pulse is detected in the control signal, e.g., by detecting a signal transition from LOW to HIGH, the modified process can start applying the machine-learning model to the real-time laparoscopic video frames and to start generating real-time decisions. Note that once the tool presence/absence decisions are being generated, the rest of the modified process is substantially the same as process 400 between step 406 and step 414.

Figures 7A, 7B:
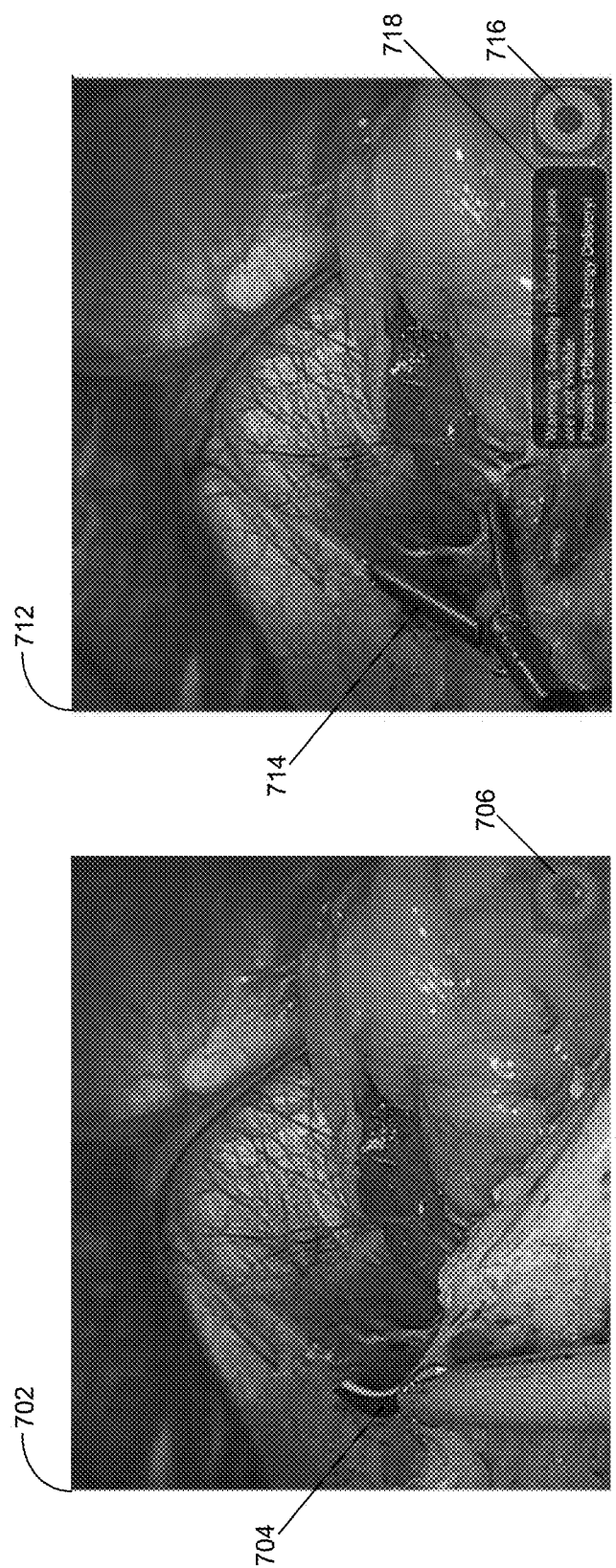
FIG. 7A shows an exemplary endoscope console displaying an endoscope image containing a target energy tool and a visual feedback generated by the disclosed energy tool presence/absence detection model in accordance with some embodiments described herein.
FIG. 7B shows an exemplary endoscope console displaying an endoscope image containing a wrong surgical tool and a visual feedback generated by the disclosed energy tool presence/absence detection model in accordance with some embodiments described herein.

FIG. 7A shows an exemplary endoscope console 702 displaying an endoscope image containing a target energy tool 704 and a visual feedback 706 generated by the disclosed energy tool presence/absence detection model in accordance with some embodiments described herein. Note that because the disclosed tool presence/absence detection model can successfully detect energy tool 704 in endoscope console 702, visual feedback 706 is shown as a green circle indicating that the tool is visible and hence safe to use.

In contrast, FIG. 7B shows an exemplary endoscope console 712 displaying an endoscope image containing a wrong surgical tool 714 and a visual feedback 716 generated by the disclosed energy tool presence/absence detection model in accordance with some embodiments described herein. Note that because the disclosed tool presence/absence detection model can successfully the target energy tool is absent in endoscope console 712 (even when a different tool 714 is present), visual feedback 716 is shown as a yellow circle indicating that an unsafe event is identified. The disclosed detection model additionally generates a warning message 718 inside endoscope console 712 next to the visual feedback 716 specifying the type of unsafe event that is detected.

Other Applications of the Energy Tool Presence/Absence Detection Model

Note that based on the ML tool-detection model output from a given surgical procedure, the total time the energy tool is present in the endoscopy video during the surgical procedure can be easily determined. Hence, a percentage of time the energy tool is present over the overall duration of the surgical duration can be calculated. This percentage value can then be compared with a standard of percentage value for the energy tool presence, and from which the skills of the surgeon using the energy tool can be estimated based on whether the computed percentage value is above or below the nominal value and by how much. For example, if a surgeon typically has 10% less "presence time" of the tool in his surgeries, this could mean that the surgeon has used less energy during the surgery and hence the patient may be able to recover faster due to less damage to the patient's tissues. Note that the energy tool presence information from the tool presence/absence detection model can be collaborated with the tool activation data from the tool log, such as the number of activations/firings of the energy tool in each minute of the determined tool presence. Note that the number of activations/firings of the tool per tool presence can be another indicator of the surgeon's skill level and/or a complexity level of the surgery. Another metric that can be determined based on the tool detection model output can include the number of activations per duration of activation. For example, 10 minutes of activation could contain 20 activations (i.e., each activation, in average, has lasted for 30 seconds). In another example, 10 minutes of activations could contain 40 activations (i.e., each activation, in average, has lasted for 15 seconds). The above metric can be used to infer the age and efficiency of the device, and can also be used to infer the complexity of the human anatomy. Note that the number of activations can also be correlated with the length of the surgery, because a higher number of activations would typically mean more damage to tissue, and hence higher likelihood of complexity which could lead to longer surgery time.

In some embodiments, the output from the disclosed ML tool presence/absence detector can be collaborated with the output from another ML model trained to detect and extract different surgical phases and surgical tasks within the surgical procedure. Hence, the disclosed ML tool presence/absence detector output can further be used to make at least the following event determinations: (1) the energy tool is present in an identified surgical phase/surgical task (such as greater curve dissection); (2) the energy tool is absence from an identified surgical phase/surgical task; (3) if the energy tool is present in an identified surgical phase/surgical task, how long the energy is present in the identified surgical phase/surgical task; (4) if the energy tool is present in an identified surgical phase/surgical task that the energy tool is not supposed to be present; and (5) if the energy tool is absent from an identified surgical phase/surgical task that the energy tool is supposed to be present. Based on the above information that can be extracted from the disclosed ML tool presence/absence detector output, the skills of the surgeon using the energy tool can be further evaluated and compared with other surgeons performing the same surgical procedure. Moreover, surgical anomalies may be identified if events (4) and (5) are detected from based on the offline procedure data analytics. Moreover, because the disclosed tool presence/absence detector can continuously report the presence and absent of the energy tool, we can count the number of times that the tool leaves the endoscope view and subsequently returns to the endoscope view. This count can be correlated with the complexity level of the organ/tissue that is under the surgery as well as the skill level of the surgeon, In some embodiments, the output from the disclosed ML tool presence/absence detector can be collaborated with the output from yet another ML model trained to detect different organs/tissues in the endoscope video of the surgical procedure. Hence, the disclosed tool presence/absence detector output can further be used to determine which organs/tissues the energy tool was used upon and for how long. Based on the above information that can be extracted from the output of the disclosed ML tool presence/absence detector, the skills of the surgeon using the energy tool can be further evaluated and compared with other surgeons performing the same surgical procedure.

In some embodiments, the output from the disclosed ML tool presence/absence detector can be collaborated with the output from yet another ML model trained to detect a bleeding event or other complication events in the endoscope video of the surgical procedure. Hence, the output of the disclosed ML tool presence/absence detector can further be used to determine if the energy tool was present during a detected bleeding event. If so, additional information related to the use of the energy tool during the surgical procedure may be collaborated with the detected event to predict or determine the cause of the bleeding. For example, the additional information of the energy tool use may include the settings, such as power level of the energy tool when the bleeding event occurs. The additional information can also include the identified surgical task detected by another ML model when the bleeding event occurs. Moreover, useful statistics can be generated in terms of what percentage of the total tool activations leads to bleeding or other complications.

Note that because the disclosed ML tool presence/absence detector was continuously trained and updated to detect different models of the energy tool with different versions (e.g., all existing versions) of a given model of the energy tool, the output from the disclosed ML tool presence/absence detector can be used during the offline procedure data analytics to generate useful statistics for the tool manufacturers. Note that the useful statistics can include collaborating above-described of bleeding and other complications statistics with the tool model/version statistics. Specifically, statistics between collected bleeding and other complication events and collected models and versions of the energy tool can be established or updated. Such statistics can then be used to evaluate and score each model and version of the energy tool.

Figure 8:
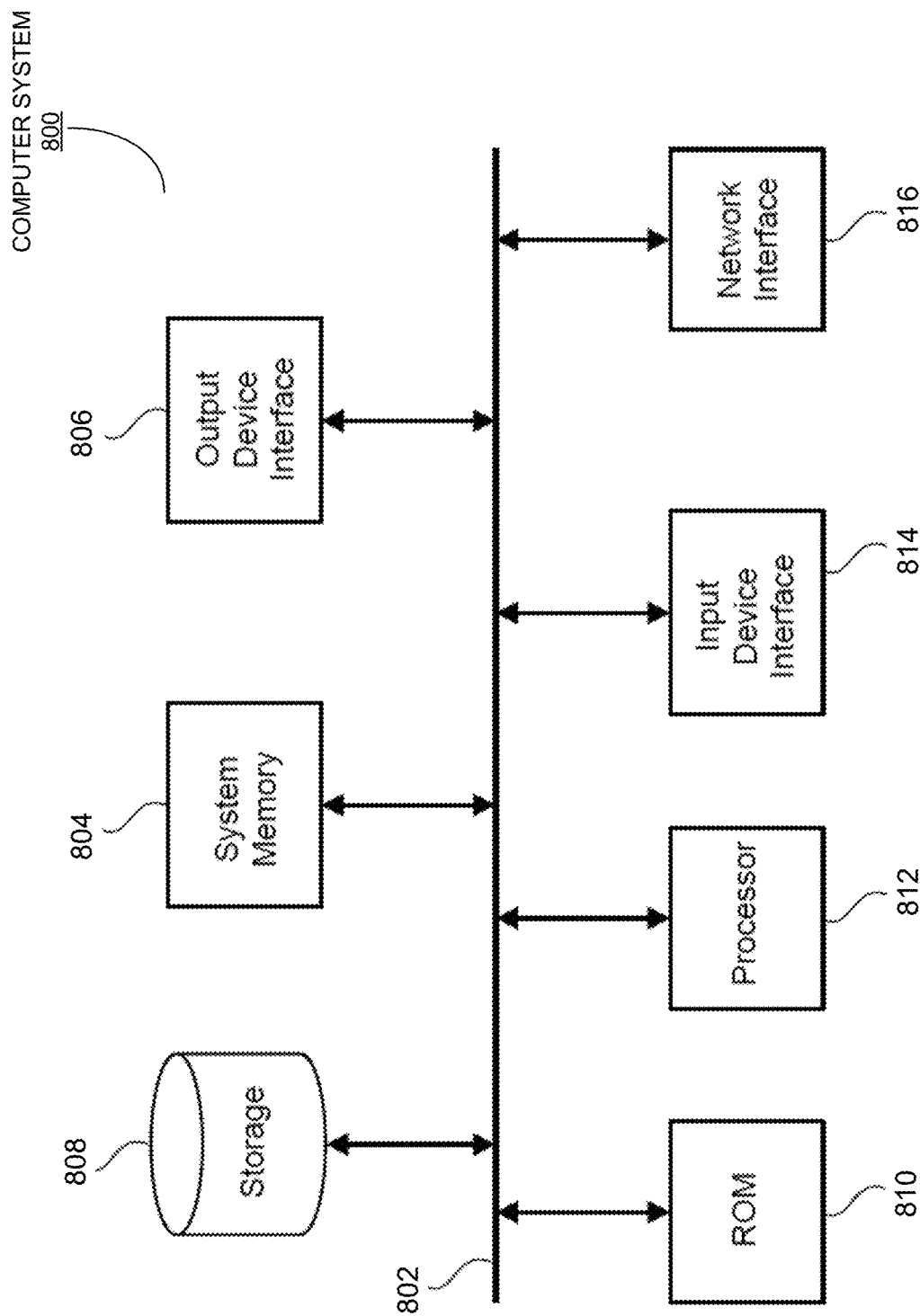
FIG. 8 conceptually illustrates a computer system with which some embodiments of the subject technology can be implemented.

FIG. 8 conceptually illustrates a computer system with which some embodiments of the subject technology can be implemented. Computer system 800 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 800 includes a bus 802, processing unit(s) 812, a system memory 804, a read-only memory (ROM) 810, a permanent storage device 808, an input device interface 814, an output device interface 806, and a network interface 816. In some embodiments, computer system 800 is a part of a robotic surgical system.

Bus 802 collectively represents all system, peripheral, and chipset buses that communicatively connect the numerous internal devices of computer system 800. For instance, bus 802 communicatively connects processing unit(s) 812 with ROM 810, system memory 804, and permanent storage device 808.

From these various memory units, processing unit(s) 812 retrieves instructions to execute and data to process in order to execute various processes described in this patent disclosure, including the above-described surgical tool presence/absence detection model building techniques and techniques for detecting unsafe events during a surgery using the disclosed surgical tool presence/absence detection models in FIGS. 1-6. The processing unit(s) 812 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 812 can be a single processor or a multi-core processor in different implementations.

ROM 810 stores static data and instructions that are needed by processing unit(s) 812 and other modules of the computer system. Permanent storage device 808, on the other hand, is a read-and-write memory device. This device is a non-volatile memory unit that stores instructions and data even when computer system 800 is off. Some implementations of the subject disclosure use a mass-storage device (such as a magnetic or optical disk and its corresponding disk drive) as permanent storage device 808.

Other implementations use a removable storage device (such as a floppy disk, flash drive, and its corresponding disk drive) as permanent storage device 808. Like permanent storage device 808, system memory 804 is a read-and-write memory device. However, unlike storage device 808, system memory 804 is a volatile read-and-write memory, such as a random access memory. System memory 804 stores some of the instructions and data that the processor needs at runtime. In some implementations, various processes described in this patent disclosure, including the above-described surgical tool presence/absence detection model building techniques and techniques for detecting unsafe events during a surgery using the disclosed surgical tool presence/absence detection models in FIGS. 1-6, are stored in system memory 804, permanent storage device 808, and/or ROM 810. From these various memory units, processing unit(s) 812 retrieves instructions to execute and data to process in order to execute the processes of some implementations.

Bus 802 also connects to input and output device interfaces 814 and 806. Input device interface 814 enables the user to communicate information to and select commands for the computer system. Input devices used with input device interface 814 include, for example, alphanumeric keyboards and pointing devices (also called "cursor control devices"). Output device interface 806 enables, for example, the display of images generated by the computer system 800. Output devices used with output device interface 806 include, for example, printers and display devices, such as cathode ray tubes (CRT) or liquid crystal displays (LCD). Some implementations include devices such as a touchscreen that functions as both input and output devices.

Finally, as shown in FIG. 8, bus 802 also couples computer system 800 to a network (not shown) through a network interface 816. In this manner, the computer can be a part of a network of computers (such as a local area network ("LAN"), a wide area network ("WAN"), an intranet, or a network of networks, such as the Internet. Any or all components of computer system 800 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for ensuring patient safety during a laparoscopic or robotic surgery involving an energy tool, the method comprising:

receiving a real-time tool control signal indicating an operating state of an energy tool during the surgery, the real-time tool control signal includes a plurality of activation pulses and wherein each activation pulse in the plurality of activation pulses corresponds to a time duration when the energy tool is activated;

simultaneously receiving real-time endoscope video images of the surgery;

simultaneously applying a machine-learning model to the real-time endoscope video images to generate real-time decisions on a location of the energy tool in the real-time endoscope video images wherein for each video frame in the real-time endoscope video images a tool presence/absence decision is generated indicating whether the energy tool is present or absent in the video frame and a confidence level associated with the tool presence/absence decision;

identifying an unsafe event in real-time by determining whenever the tool presence/absence decision is a tool absence decision that coincides with an activation pulse of the plurality of activation pulses; and taking a proper action when the unsafe event is identified.

2. The computer-implemented method of claim 1, wherein the energy tool is an ultrasonic energy tool for cutting and sealing tissues at the same time using two jaws, and wherein the machine-learning model is trained to generate a tool presence decision for a video frame only when both of the two jaws are detected in the video frame.

3. The computer-implemented method of claim 1 wherein identifying the unsafe event further comprises determining if the tool absence decision is at the beginning of the time duration of the activation pulse in the real-time tool control signal; and if so, determining that the unsafe event is identified;

otherwise, determining that the energy tool is safe to use.

4. The computer-implemented method of claim 3, wherein if the tool absence decision does not coincide with any activation pulse in the real-time tool control signal, the method further comprises determining that the energy tool is safe to use.

5. The computer-implemented method of claim 1, wherein taking the proper action when the unsafe event is identified includes:

if the confidence level is above a high confidence level threshold, immediately disabling the energy tool; and if the confidence level is below the high confidence level threshold, taking one or more actions selected from the following options without disabling the energy tool:

displaying a visual alert on an endoscope monitor;

generating an audio alert;

generating a mechanical vibration through the energy tool; and delaying the firing of the energy tool until a user takes a further action on the energy tool.

6. A system for ensuring patient safety during a laparoscopic or robotic surgery involving an energy tool, the system comprising:

one or more processors; and a memory coupled to the one or more processors, the memory storing instructions that, when executed by the one or more processors, cause the system to:

receive a real-time tool control signal indicating an operating state of an energy tool during the surgery, the real-time tool control signal includes a plurality of activation pulses, each activation pulse represents a time duration when the energy tool is activated;

simultaneously receive real-time endoscope video images of the surgery;

simultaneously apply a machine-learning model to the real-time endoscope video images to generate real-time decisions on a location of the energy tool in the real-time endoscope video images wherein for each video frame in the real-time endoscope video images a tool presence/absence decision is generated indicating whether the energy tool is present or absent in the video frame and a confidence level associated with the tool presence/absence decision;

identifying an unsafe event by determining when the tool presence/absence decision is a tool absence decision that coincides with an activation pulse of the plurality of activation pulses; and take a proper action when the unsafe event is identified.

7. The system of claim 6, wherein the energy tool is an ultrasonic energy tool for cutting and sealing tissues at the same time using two jaws, and wherein the machine-learning model is trained to generate a tool presence decision for a video frame only when both of the two jaws are detected in the video frame.

8. The system of claim 6, wherein the memory further stores instructions that, when executed by the one or more processors, cause the system to identify the unsafe event by:

determining if the tool absence decision is at the beginning of the time duration of the activation pulse in the real-time tool control signal; and if so, determining that the unsafe event is identified;

otherwise, determining that the energy tool is safe to use.

9. The system of claim 8, wherein if the tool absence decision does not coincide with any activation pulse in the real-time tool control signal, the system determines that the energy tool is safe to use.

10. The system of claim 6, wherein the memory further stores instructions that, when executed by the one or more processors, cause the system to take the proper action when the unsafe event is identified by:

immediately disabling the energy tool if the confidence level is above a high confidence level threshold; and taking one or more actions selected from the following options without disabling the energy tool if the confidence level is below the high confidence level threshold:

displaying a visual alert on an endoscope monitor;

generating an audio alert;

generating a mechanical vibration through the energy tool; and delaying the firing of the energy tool until a user takes a further action on the energy tool.

11. An ultrasonic or bipolar tissue cutting/cauterizing surgical system, the surgical system comprising:

a signal and power generator;

an energy tool;

one or more processors; and a memory coupled to the one or more processors, the memory storing instructions that, when executed by the one or more processors, cause the surgical system to:

receive a real-time tool control signal from the generator, wherein the real-time tool control signal indicates an operating state of the energy tool during a surgery, the real-time tool control signal includes a plurality of activation pulses, each activation pulse represents a time duration when the energy tool is activated;

simultaneously receive real-time endoscope video images of the surgery;

simultaneously apply a machine-learning model to the real-time endoscope video images to generate real-time decisions on a location of the energy tool in the real-time endoscope video images wherein for each video frame in the real-time endoscope video images a tool presence/absence decision is generated indicating whether the energy tool is present or absent in the video frame and a confidence level associated with the tool presence/absence decision;

identify an unsafe event by determining when the tool presence/absence decision is a tool absence decision that coincides with an activation pulse of the plurality of activation pulses; and take a proper action when the unsafe event is identified.

12. The surgical system of claim 11, wherein the energy tool is an ultrasonic energy tool for cutting and sealing tissues at the same time using two jaws, and wherein the machine-learning model is trained to generate a tool presence decision for a video frame only when both of the two jaws are detected in the video frame.

13. The surgical system of claim 11, wherein the memory further stores instructions that, when executed by the one or more processors, cause the surgical system to identify the unsafe event by:

determining if the tool absence decision is at the beginning of the time duration of the activation pulse in the real-time tool control signal; and if so, determining that the unsafe event is identified;

otherwise, determining that the energy tool is safe to use.

\* \* \* \* \*